(12) United States Patent
Hruska et al.

(10) Patent No.: US 6,540,757 B1
(45) Date of Patent: Apr. 1, 2003

(54) CARTRIDGE FOR USE IN A DERMAL ABRASION SYSTEM

(75) Inventors: Thomas Hruska, Laguna Woods, CA (US); Brent Allen, Rancho SantaMargarita, CA (US)

(73) Assignee: James C. Fallon, Laguna Niguel, CA (US)

(*) Notice: Subject to any disclaimer, the term of this patent is extended or adjusted under 35 U.S.C. 154(b) by 0 days.

(21) Appl. No.: 09/904,708

(22) Filed: Jul. 13, 2001

(51) Int. Cl.[7] .............................................. A61B 17/50
(52) U.S. Cl. ............................ 606/131; 451/2; 604/289
(58) Field of Search ................................. 606/131, 132, 606/133; 604/290, 310, 35, 289; 132/73, 76.4, 76.5; 451/2, 87

(56) References Cited

U.S. PATENT DOCUMENTS 5,971,999 A * 10/1999 Naldoni ..................... 451/87
6,080,165 A * 6/2000 DeJacma .................... 606/131
6,183,483 B1 * 2/2001 Chang ........................ 606/131
6,247,997 B1 * 6/2001 Khalaj ............................ 451/2
6,299,620 B1 * 10/2001 Shadduck et al. .......... 604/289
6,432,113 B1 * 8/2002 Parkin et al. ................. 604/22

* cited by examiner

Primary Examiner—Pedro Philogene
(74) Attorney, Agent, or Firm—Richard R. Muccino

(57) ABSTRACT

The present invention is directed to a cartridge for use in a dermal abrasion system. The cartridge comprises a supply compartment and a waste compartment. The front side of the supply compartment comprises an air inlet fitting for introducing air into the supply compartment and the bottom side of the supply compartment comprises a feed tube fitting. The front side of the waste compartment comprises a vacuum inlet fitting for introducing vacuum into the waste compartment and the front side of the waste compartment comprises a return tube fitting. The present invention also includes an apparatus for use in a dermal abrasion system employing the novel cartridge and a method for removing debris in a dermal abrasion system with the novel cartridge.

22 Claims, 2 Drawing Sheets

CARTRIDGE FOR USE IN A DERMAL ABRASION SYSTEM

FIELD OF THE INVENTION

The present invention is directed to a cartridge for use in a dermal abrasion system. The cartridge comprises a supply compartment and a waste compartment. The front side of the supply compartment comprises an air inlet fitting for introducing air into the supply compartment and the bottom side of the supply compartment comprises a feed tube fitting. The front side of the waste compartment comprises a vacuum inlet fitting for introducing vacuum into the waste compartment and the front side of the waste compartment comprises a return tube fitting. The present invention also includes an apparatus for use in a dermal abrasion system employing the novel cartridge and a method for removing debris in a dermal abrasion system with the novel cartridge.

DESCRIPTION OF THE BACKGROUND

Dermal abrasion systems are used to remove a surface portion of skin to obtain aesthetic improvements in such areas as scars subsequent to a surgical procedure, burns, acne, scars received from photo sensitizing agents, small surface roughness on the face, and the like. Dermal abrasion systems apply a controlled application of a mixture of air and a granular abrasive substance, such as aluminum oxide, to the skin to obtain a superficial abrasion of adjustable magnitude. The dermal abrasion systems generally comprise an air supply, a vacuum supply, a cartridge for a granular abrasive substance, a hand tool to be applied to the surface of skin, and a waste collection canister for receiving the used abrasive substance and the removed portions of surface tissue from the skin. The abrasion may be of minimum value, such as a "peeling" involving the removal of the outer-most layers of the epidermis, or may be of maximum value, such as a deep abrasion involving the dermis.

U.S. Pat. No. 3,750,909 (Butler) discloses an aerosol dispenser having a main valve and an auxiliary valve to clean out the nozzle coupled to the main valve. After use, nozzle 16 is removed from main valve 40 (FIG. 2) and coupled to auxiliary valve 56 (FIG. 3). By depressing the nozzle on the auxiliary valve, pressurized gas is forced through the nozzle cleaning it out. Specifically, the aerosol container comprises a closed container having a flowable material and pressurized gas for propelling the material out of the container. A main valve is mounted on the container above the level of the material and is connected to a tube which extends downward below the level of material. The main valve is normally open to allow the gas to propel the material through the tube and the valve out of the container. A nozzle is mounted on the main valve and coupled to direct the material out of the container. An auxiliary valve is provided in the container at a location at which the valve can be placed in direct communication with the gas. The nozzle can be cleaned out by the pressurized gas when the nozzle is coupled to the auxiliary valve and the valve is opened.

U.S. Pat. No. 4,358,027 (Poitras) discloses a liquid dispenser apparatus for dispensing metered quantities of a liquid. The apparatus comprises a container for the liquid to be dispensed and a pump having a cylinder with inlet and outlet ports which is manually reciprocal between an intake stroke, during which liquid is drawn through the inlet port, and a discharge stroke, during which the entire liquid content of the cylinder is expelled through the outlet port. The pump has a pump rod fixed to the piston and extends out of the cylinder to produce the intake and discharge strokes. A manual selector limiter is provided for adjusting the maximum length of the discharge stroke. The limiter has a slidable stop mounted on the pump rod so as to limit the discharge stroke and establish the volume of liquid drawn into the cylinder during the intake stroke. A fastener is supported by the stop and is movable between a locked position and a release position that allows the movement. An activator moves the fastener between the locked and release positions. An abutment surface on the cylinder engages the stop to limit the discharge stroke. The activator is operable to overcome the bias and force the fastener into the release position. The manual valve selectively opens and closes the inlet and outlet ports.

U.S. Pat. No. 5,050,782 (Cheng) discloses a measured volume liquid dispenser having an elongated barrel and plunger slidably mounted within a cylindrical bore in the barrel. The barrel has an inlet check valve located at the bottom of the cylindrical bore so that liquid may be drawn into the bore during an up-stroke of the plunger. The plunger has an axial passage and an outlet check valve in the passage. The outlet check valve allows liquid to be dispensed as the plunger is depressed in a downstroke in the barrel but provides a seal during the plunger upstroke so that the liquid may be drawn into the cylindrical bore through the inlet check valve.

U.S. Pat. No. 5,141,137 (Knodel) discloses a volumetric device for dispensing a predetermined volume of fluid from a fluid reservoir. The device includes a valve head mounted to a reservoir and a piston-valve pump mounted on the valve head. An intake valve and a discharge valve are each mounted to the valve head and are connected to the piston valve pump. Upon actuation of the piston valve pump, fluid is pumped from the reservoir through the intake valve and the valve head to the discharge valve. A ventilation valve has a first duct in the valve head connecting a blocking side of the ventilation valve to ambient atmosphere and a second duct connecting an opposite side of the ventilation valve with the reservoir. The ventilation valve is a check valve with a borehole in the direction of the vertical axis of the valve head. A free valve element is inserted into the borehole and is actuated by gravity toward sealing of a valve seat.

U.S. Pat. No. 5,254,108 (Burrell et al.) discloses a liquid applicator designed to be supported by hand for applying a liquid to a surface. The applicator has a handle which supports a roller equipped with a cam track and cam follower which reciprocates a piston within a cylinder to pump liquid to a nozzle metered with rotation of the roller.

U.S. Pat. No. 5,441,490 (Svedman) discloses an apparatus for use in the transdermal perfusion of fluids through the skin of a human. The apparatus has a housing attachable to the body with a contact surface held in contact with a portion of skin. The housing is a chamber and the contact surface is an aperture connected to the chamber. A fluid supply provides a perfusion phase and a de-epithelializing element provides for removal of a portion of epidermis. The de-epithelializing element exposes an area of dermis of the skin at a treatment site which is accessible via the aperture so that during the perfusion phase direct contact is made between the fluid in the chamber and the dermis.

U.S. Pat. No. 5,489,280 (Russell) discloses a fluid applicator configured to massage and irrigate a surgical site on a patient's skin. The applicator has a fluid reservoir for irrigating the surgical site and a collector for collecting irrigation fluids from the surgical site. A motor assembly is connected to the fluid reservoir for expelling a fluid in the reservoir and irrigating the surgical site. The fluid reservoir has a nozzle for directing the fluid from the fluid reservoir to the surgical site. The collector has a sponge connected to the fluid reservoir for engaging the surgical site when the applicator is used to massage and irrigate the surgical site. A means for returning fluids collected by the collector to the fluid reservoir is included.

U.S. Pat. No. 5,697,920 (Gibbons) discloses a device for cleaning the skin and its appendages. The device comprises a brush portion having soft bristles and two conduits. The first conduit has a connector distal to the brush for connection to a solution source and at the end proximal to the brush delivers the solution into the brush above the bristles. The second conduit has a negative pressure source and a first opening into the brush near the bristles of the brush.

U.S. Pat. No. 5,782,871 (Fujiwara et al.) discloses a sampling device of a suction effusion fluid which includes a cell having a vacuum suction port and a skin suction port. The vacuum suction port is connected to a vacuum source and the skin suction port is opposite to a skin surface. A slide valve in the cell is movable parallel to the skin surface and is used for opening or closing a path connecting the skin suction port with the vacuum suction port without releasing the vacuum source. Fluid reservoirs in the slide valve alternately connect with the skin suction port and the vacuum suction port through the slide valve. The fluid reservoirs store an effusion fluid from the skin surface by vacuum suction through the skin suction port. When the slide valve is moved to a position where a fluid reservoir is connected with the skin suction port and the vacuum suction port, one of the remaining fluid reservoirs is exposed to the outside of the cell.

U.S. Pat. No. 5,787,928 (Allen et al.) discloses a valve having a housing and a component movable within the housing. The housing has a first, second, third, fourth, and fifth ports and the movable component has a first passageway. A first orientation of the movable component within the housing connects the first port through the first passageway to the second port. A second orientation of the movable component within the housing connects the second port through the first passageway to the third port. A second passageway is defined between the housing and the movable component. The fourth port and fifth port are connected to the second passageway at both the first and second orientations of the movable component. The fourth port comprises a first slot shaped opening facing the movable component.

U.S. Pat. No. 5,843,052 (Benja-Athon) discloses a compact irrigation and sterilization kit to cleanse and debride damaged structure such as a wound. The irrigation tubing kit has a flexible conduit having a coupling to attach the tubing kit to a faucet. A filter eliminates impurities from the flowing fluid from the faucet. A flow-regulating valve regulates the volume of the filter fluid flowing in the conduit. A short semi-rigid tubing extension with a short conduit and an opening is coupled to a vial of chemicals and medications to admit the chemicals and medications into the conduit. The flow of the chemicals and medications is regulated by another flow-regulating valve. Another short semi-rigid bypass port extension with a short conduit and an opening introduces fluids and chemical substances into the conduit of the tubing kit beyond the filter. A disperser distributes the chemical, medications and fluid over the wound. A reservoir which stores chemicals and medications prior to the application of the tubing kit delivers the chemicals and medications into the conduit of the tubing kit. The flowing fluid from a faucet flows through the coupling, filter and flow-regulating valve and provides the force to generate filtered fluid to remove foreign bodies from and to dispense the chemicals and medications from the reservoir directly into the conduit to sterilize the wound.

U.S. Pat. No. 5,848,998 (Marasco, Jr.) discloses a method for treating a body wound site on a patient which comprises applying a flexible transparent envelope about the wound site of the patient. The envelope has at least one primary opening with a peripheral lip to permit attachment of the envelope to the patient. A drain is connected to the envelope and a movable hand manipulatable fluid applying tissue treatment gun is introduced into the envelope. A fluid is sprayed into the envelope from the hand manipulable gun against the wound site for treatment of the patient. The envelope is spaced from the wound site by introducing a pressurized gas into the envelope. The pressurized gas is within the envelope during extended periods of fluid treatment and periods of absence of fluid treatment to prevent the envelope from contacting the wound site and to maintain the sterility of the wound site.

U.S. Pat. No. 5,862,958 (Edwards et al.) discloses a dispenser for connection to a mouth of a container for dispensing a liquid from the container. The dispenser comprises a dispensing fluid path connected to a dispensing orifice, a return fluid path connected to the liquid in the container, a cylinder having one end connected with the liquid in the container, and a plunger slidably mounted in the cylinder. Retracting the plunger in the cylinder moves the liquid from the container into the one end of the cylinder. A flow control valve has a path connecting one end of the cylinder and a control valve outlet and is movable between a first position placing the control valve outlet in connection with the dispensing path, whereby advancing the plunger in the cylinder moves the liquid from one end of the cylinder and out the dispensing orifice, and a second position placing the control valve outlet in connection with the return path, whereby advancing the plunger in the cylinder moves the liquid from the one end of the cylinder and back into the container. A first check valve in the control valve fluid path within the flow control valve permits a flow of the liquid from the one end of the cylinder to the control valve outlet and prevents the flow of liquid from the control valve outlet back into the one end of the cylinder. A second check valve is in the main passage and permits the liquid to flow from the container into the cylinder and prevents the liquid from flowing from the one end of the cylinder back into the container.

U.S. Pat. No. 5,037,432 (Molinari) discloses a hand tool for removing skin by superficial abrasion with a mixture of air and a granular abrasive substance. The tool has an elongated manipulative body, a supply tube for the mixture, and a collection tube for the mixture and the removed portions of skin. Each tube has an operating head secured to the manipulative body. The head has a longitudinal axis and a wall with a portion inclined and offset with respect to the axis. A throughhole in the wall portion internally connects with the free ends of the terminal portions of the supply tube. The throughhole is aligned with the terminal portion of the supply tube so that by keeping in contact the throughhole with the surface, the stream of mixture travelling through the terminal portion of the supply tube and the throughhole is caused to strike the surface with an inclined incident angle.

IN THE FIGURES

SUMMARY OF THE INVENTION

Figure 1:
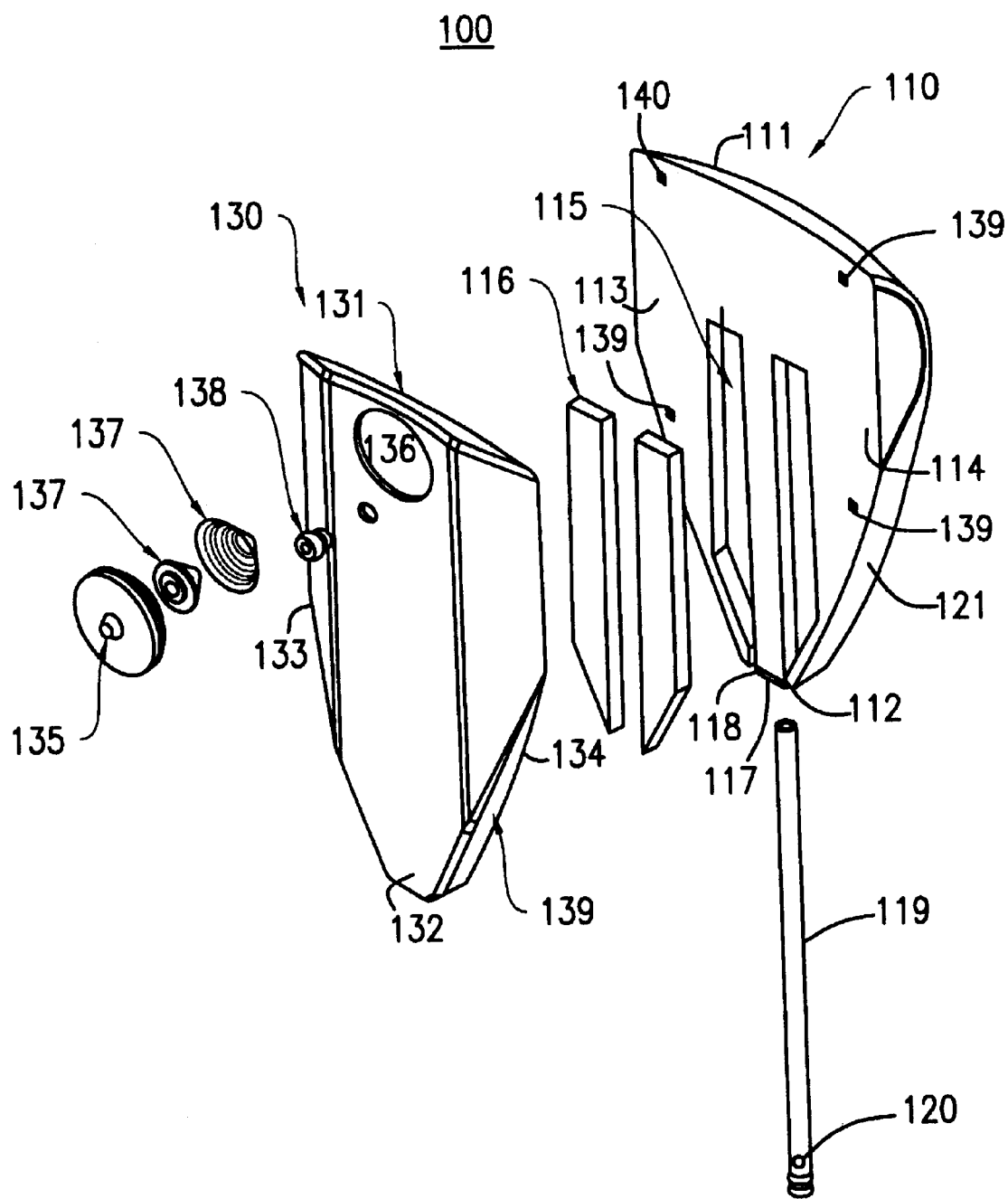
FIG. 1 illustrates a cartridge for use in a dermal abrasion system in a preferred embodiment of the present invention.

The present invention is directed to a cartridge for use in a dermal abrasion system comprising:

(a) a supply compartment having a top, bottom, front, and a back side, wherein the front side of the supply compartment comprises an air inlet fitting for introducing air into the supply compartment and the bottom side of the supply compartment comprises a feed tube fitting; and (b) a waste compartment having a top, bottom, front, and a back side, wherein the front side of the waste compartment comprises a vacuum inlet fitting for introducing vacuum into the waste compartment and the front side of the waste compartment comprises a return tube fitting.

In another embodiment, the invention is directed to an apparatus for use in a dermal abrasion system comprising:

(A) a cartridge comprising:

(a) a supply compartment having a top, bottom, front, and a back side, wherein the front side of the supply compartment comprises an air inlet fitting for introducing air into the supply compartment and the bottom side of the supply compartment comprises a feed tube fitting; and (b) a waste compartment having a top, bottom, front, and a back side, wherein the front side of the waste compartment comprises a vacuum inlet fitting for introducing vacuum into the waste compartment and the front side of the waste compartment comprises a return tube fitting;

(B) a granular abrasive substance inside the supply compartment;

(C) a vacuum supply attached to the vacuum inlet fitting of the waste compartment;

(D) a hand tool to be applied to the surface of skin attached to the feed tube fitting of the supply compartment; and (E) duct means from the feed tube fitting to the hand tool for conveying a mixture of air and granular abrasive substance from the supply compartment to the hand tool, duct means from the hand tool to the return tube fitting for conveying a mixture of air and granular abrasive substance and removed portions of skin waste from the hand tool to the waste compartment, and duct means from the vacuum inlet fitting in the waste compartment to the vacuum supply.

In yet another embodiment, the invention is directed to a method for removing debris in a dermal abrasion system which comprises the steps of:

(1) providing an apparatus comprising:

(A) a cartridge comprising:

(a) a supply compartment having a top, bottom, front, and a back side, wherein the front side of the supply compartment comprises an air inlet fitting for introducing air into the supply compartment and the bottom side of the supply compartment comprises a feed tube fitting; and (b) a waste compartment having a top, bottom, front, and a back side, wherein the front side of the waste compartment comprises a vacuum inlet fitting for introducing vacuum into the waste compartment and the front side of the waste compartment comprises a return tube fitting;

(B) a granular abrasive substance inside the supply compartment;

(C) a vacuum supply attached to the vacuum inlet fitting of the waste compartment;

(D) a hand tool to be applied to the surface of skin attached to the feed tube fitting of the supply compartment; and (E) duct means from the feed tube fitting to the hand tool for conveying a mixture of air and granular abrasive substance from the supply compartment to the hand tool, duct means from the hand tool to the return tube fitting for conveying a mixture of air and granular abrasive substance and removed portions of skin waste from the hand tool to the waste compartment, and duct means from the vacuum inlet fitting in the waste compartment to the vacuum supply;

(2) applying vacuum to the vacuum inlet fitting to introduce vacuum into the waste compartment thereby drawing the granular abrasive substance in the supply compartment into the feed tube fitting and the hand tool.

DETAILED DESCRIPTION OF THE INVENTION

The present invention is directed to a cartridge for use in a dermal abrasion system. The cartridge comprises a supply compartment and a waste compartment. The front side of the supply compartment comprises an air inlet fitting for introducing air into the supply compartment and the bottom side of the supply compartment comprises a feed tube fitting. The front side of the waste compartment comprises a vacuum inlet fitting for introducing vacuum into the waste compartment and the front side of the waste compartment comprises a return tube fitting. The present invention also includes an apparatus for use in a dermal abrasion system employing the novel cartridge and a method for removing debris in a dermal abrasion system with the novel cartridge.

The cartridge for use in a dermal abrasion system of the present invention is a precharged (containing clean crystals) transparent cartridge that is a total closed loop microdermabrasion system. The cartridge is a sealed system that when loaded onto the machine, breaks the hermetically sealed tube when pierced by the machine's spike. This allows the fresh crystals to flow down the feed tube, through the hand tool tube and hand tool onto the patient's skin. The cartridge contains a waste cartridge filter, air intake filter, a velocity feed tube, a supply compartment for clean crystals, and a waste compartment for the collection of the used crystal, skin, bacteria, and viruses. The shape of the cartridge is important because its inwardly sloped sides insure that the crystals, using gravity, flow to the bottom of the cartridge. The multiple air intake holes serve two purposes. First, the multiple air intake holes serve to regulate the vacuum within the cartridge. Secondly, the multiple air intake holes serve to serrate the clean crystals, thereby dispersing them, preventing them from clumping together which would cause the machine to malfunction. The transparent plastic design allows the operator to know when the cartridge is empty and needs replacement. This limited use cartridge is discarded after several uses and a new one is then reloaded onto the machine.

The invention will be better understood from the following detailed description of the preferred embodiments taken in conjunction with the Figures, in which like elements are represented by like referenced numerals.

FIG. 1 illustrates a cartridge for use in a dermal abrasion system in a preferred embodiment of the present invention. In FIG. 1, the cartridge is depicted generally as 100 and is constructed in accordance with a preferred embodiment of the present invention. The cartridge 100 for use in a dermal abrasion system comprises a supply compartment 110 and a waste compartment 130.

Supply compartment 110 includes a top 111, bottom 112, front 113, and a back side 114. The front side 113 of the supply compartment 110 comprises an air inlet fitting 115 for introducing air into the supply compartment. Preferably, the air inlet fitting 115 comprises multiple air intake holes, as shown. The air inlet fitting 115 may further comprise an air intake filter 116. The bottom side 112 of the supply compartment comprises a feed tube fitting 117. The feed tube fitting 117 may further comprise a seal 118. The feed tube fitting 117 is adapted to mate with a feed tube 119, which may contain a metering hole 120. The sides of the supply compartment preferably slope inwardly 121. The supply compartment may further comprise a granular abrasive substance 122 (not shown).

Waste compartment 130 includes a top 131, bottom 132, front 133, and a back side 134. The front side 133 of the waste compartment 130 comprises a vacuum inlet fitting 135 for introducing vacuum into the waste compartment. The vacuum inlet fitting 135 is connected to a hole 136 in the waste compartment 130 and may further comprise one or more air outtake filters 137. The front side of the waste compartment comprises a return tube fitting 138. The sides of the waste compartment preferably slope inwardly 139. The supply compartment 110 and the waste compartment 130 are preferably attached to each other such as through alignment tabs and glue joints 140. The supply compartment and the waste compartment are preferably transparent.

As set out above, the cartridge 100 for use in a dermal abrasion system comprises a supply compartment 110 and a waste compartment 130. Preferably, the cartridge is a single disposable cartridge. The supply compartment 110 of the cartridge comprises an inlet air filter 116, a feed tube 119, and aeration holes 115. The air intake filter 116 filters the free air entering the supply compartment 110. The air inlet fitting 115 allows a vacuum to enter the supply compartment 110, which allows the abrasive media to be pulled out of the supply compartment 110 via a feed tube fitting 117. The feed tube fitting 117 is located at the bottom of the supply compartment 110 and extends upward in a straw type fashion. There is a small metering hole 120 in the side of the feed tube 119 located at the bottom. The metering hole 120 allows only a measurable amount of abrasive material to be pulled from the supply compartment 110 of the cartridge 100. The remainder of the vacuum is drawn from the top of the feed tube fitting 117, which will assist in pulling the abrasive media through the supply compartment 110.

The waste compartment 130 of the disposable cartridge 100 comprises a vacuum inlet fitting 135 and an outlet air filter 136. After the air flows through the system, the air returns back to the cartridge. The air enters the waste compartment 130 of the vacuum inlet fitting 135, through a hole 136 located in the back top area 131. The vacuum inlet fitting 135 prevents air leaks as the air passes from the machine to the waste compartment 130. Preferably, there is a baffle (not shown) at the back side 134 located top center and runs through half the waste safe of the length of the length. The air will hit the baffle causing the heavy particles (abrasive media and removed skin) to fall to the bottom of the waste compartment 130. The air then exits the waste compartment 130 via another small hole 136 in the back top area. There is an air inlet filter 137 which stops particles from leaving the waste compartment 130 and entering the vacuum pump (not shown).

In a preferred embodiment, the cartridge 100 further comprises a hand tool connected to the feed tube fitting through a duct. The hand tool comprises an elongated manipulative body, a supply tube for a mixture of air and a granular abrasive substance, and a collection tube for vacuuming in the mixture and removed portions of skin. Each tube has a terminal portion with a free end, and an operating head secured to the manipulative body at the distal end and housing the terminal portions. The body houses the other portion of the tubes. The head has a longitudinal axis and is provided with a wall having a wall portion inclined and offset with respect to the axis. A throughhole is provided in the wall portion and internally communicates with the free ends of the terminal portions. The throughhole is aligned with the terminal portion of the supply tube so that, by keeping in contact the throughhole with the surface, the stream of mixture travelling through the terminal portion of the supply tube and the throughhole is caused to strike the surface with an inclined incident angle.

Figure 2:
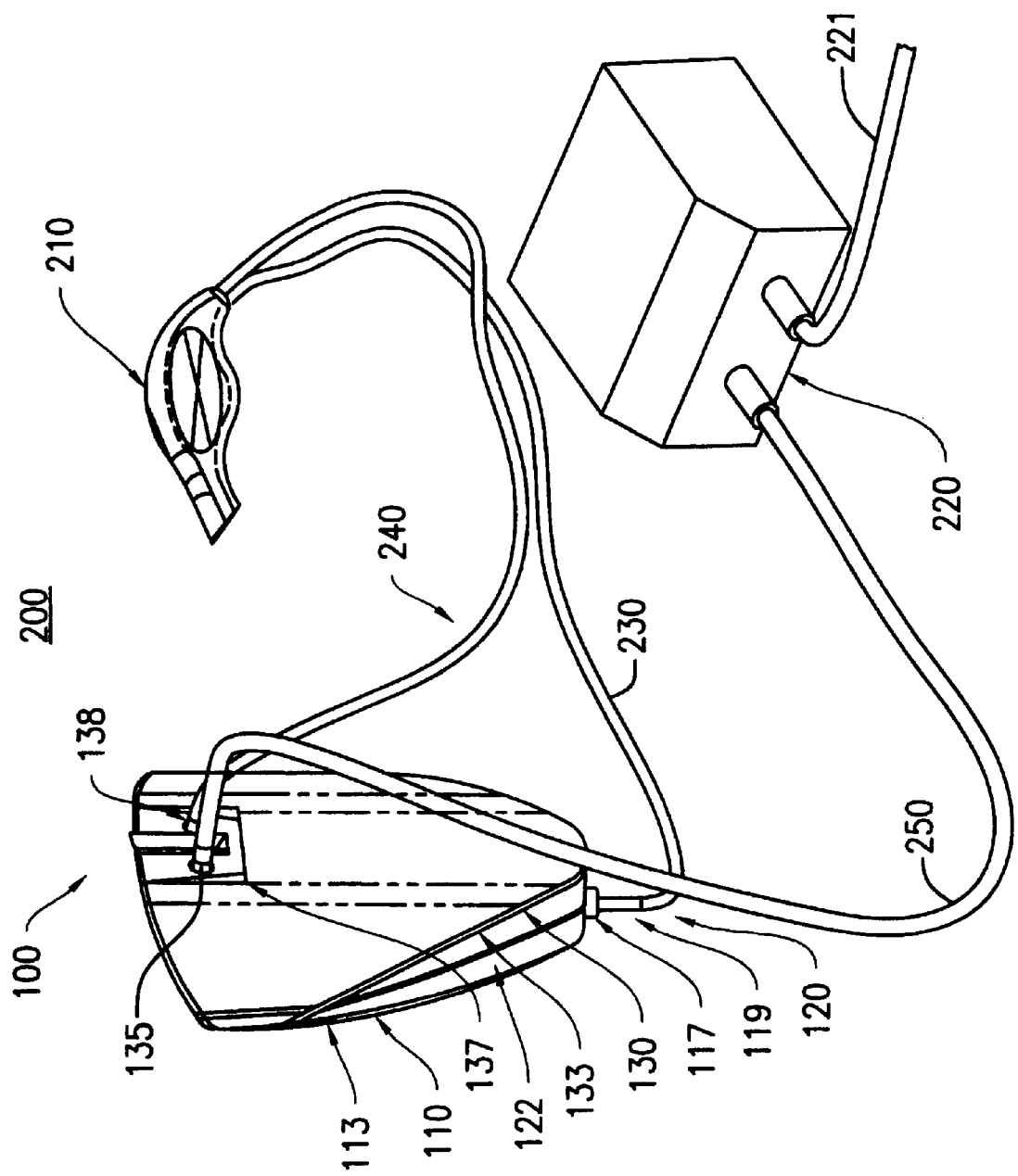
FIG. 2 illustrates an apparatus for use in a dermal abrasion system in a preferred embodiment of the present invention.

FIG. 2 illustrates an apparatus for use in a dermal abrasion system in a preferred embodiment of the present invention. In FIG. 2, the apparatus is depicted generally as 200 and is constructed in accordance with a preferred embodiment of the present invention. The apparatus 200 for use in a dermal abrasion system comprises a cartridge 100, a hand tool 210, a vacuum supply 220, duct means 230 from cartridge 100 to hand tool 210, duct means 240 from hand tool 210 to cartridge 100, and duct means 250 from cartridge 100 to vacuum supply 220.

The cartridge 100 for use in a dermal abrasion system has a supply compartment 110 and a waste compartment 130.

Supply compartment 110 includes a top 111, bottom 112, front 113, and a back side 114 (shown in detail in FIG. 1). The front side 113 of the supply compartment 110 comprises an air inlet fitting 115 (shown in detail in FIG. 1) for introducing air into the supply compartment 110. Preferably, the air inlet fitting 115 comprises multiple air intake holes (shown in detail in FIG. 1). The air inlet fitting 115 may further comprise an air intake filter 116 (shown in detail in FIG. 1). The bottom side 112 of the supply compartment comprises a feed tube fitting 117 adapted to mate with a feed tube 119, which may contain a metering hole 120. The sides of the supply compartment preferably slope inwardly (shown in FIG. 1). The supply compartment contains a granular abrasive substance 122 (not shown).

Waste compartment 130 includes a top 131, bottom 132, front 133, and a back side 134 (shown in detail in FIG. 1). The front side 133 of the waste compartment 130 comprises a vacuum inlet fitting 135 for introducing vacuum into the waste compartment. The vacuum inlet fitting 135 is connected to a hole 136 (shown in detail in FIG. 1) in the waste compartment 130 and may further comprise one or more air outtake filters 137 (shown in detail in FIG. 1). The front side of the waste compartment 130 comprises a return tube fitting 138. The sides of the waste compartment preferably slope inwardly. The supply compartment 110 and the waste compartment 130 are attached to each other and are preferably transparent.

Vacuum supply 220 is attached to the vacuum inlet fitting 135 of the waste compartment 130. Hand tool 210, applied to the surface of skin, is attached to the feed tube fitting 138 of the supply compartment 110. Duct means 230 from the feed tube fitting 138 to the hand tool 210 conveys a mixture of air and granular abrasive substance from the supply compartment 110 to the hand tool 210. Duct means 240 from the hand tool 210 to the return tube fitting 138 conveys a mixture of air and granular abrasive substance and removed portions of skin waste from the hand tool 210 to the waste compartment 130. Duct means 250 from the vacuum inlet fitting 135 in the waste compartment 130 to the vacuum supply 220. Vacuum supply may optionally have a duct means 221 to exhaust air.

In another preferred embodiment, the present invention pertains to a method for removing debris in a dermal abrasion system which comprises the steps of:

(1) providing an apparatus comprising:
   (A) a cartridge comprising:
      (a) a supply compartment having a top, bottom, front, and a back side, wherein the front side of the supply compartment comprises an air inlet fitting for introducing air into the supply compartment and the bottom side of the supply compartment comprises a feed tube fitting; and
      (b) a waste compartment having a top, bottom, front, and a back side, wherein the front side of the waste compartment comprises a vacuum inlet fitting for introducing vacuum into the waste compartment and the front side of the waste compartment comprises a return tube fitting;
   (B) a granular abrasive substance inside the supply compartment;
   (C) a vacuum supply attached to the vacuum inlet fitting of the waste compartment;
   (D) a hand tool to be applied to the surface of skin attached to the feed tube fitting of the supply compartment; and
   (E) duct means from the feed tube fitting to the hand tool for conveying a mixture of air and granular abrasive substance from the supply compartment to the hand tool, duct means from the hand tool to the return tube fitting for conveying a mixture of air and granular abrasive substance and removed portions of skin waste from the hand tool to the waste compartment, and duct means from the vacuum inlet fitting in the waste compartment to the vacuum supply;

(2) applying vacuum to the vacuum inlet fitting to introduce vacuum into the waste compartment thereby drawing the granular abrasive substance in the supply compartment into the feed tube fitting and the hand tool.

In a preferred embodiment, the apparatus further comprises a hand tool connected to the feed tube fitting through a duct. The hand tool comprises an elongated manipulative body, a supply tube for a mixture of air and a granular abrasive substance, and a collection tube for vacuuming in the mixture and removed portions of skin. Each tube has a terminal portion with a free end, and an operating head secured to the manipulative body at the distal end and housing the terminal portions. The body houses the other portion of the tubes. The head has a longitudinal axis and is provided with a wall having a wall portion inclined and offset with respect to the axis. A throughhole is provided in the wall portion and internally communicates with the free ends of the terminal portions. The throughhole is aligned with the terminal portion of the supply tube so that, by keeping in contact the throughhole with the surface, the stream of mixture travelling through the terminal portion of the supply tube and the throughhole is caused to strike the surface with an inclined incident angle.

The hand tool has a cylindrical structure comprising a cylindrical body surmounted by a coaxial bell-like element having a bottom wall delimited by a pair of spherical surfaces. A portion of the bottom wall, inclined with respect to the longitudinal axis of the bell-like element, is provided with a throughhole, which is offset from the axis of the element with a throughhole disposed off-set from the axis in a bottom wall of the element delimited by a pair of spherical surfaces. This wall is laid over the skin to be treated so that the hole faces the region in which the tissue portions must be removed. Through this hole the granular abrasive substances exit under the thrust of the compressed air provided by the pressurized fluid generator, causing removal of the portions of tissue in the amount desired by the operator. Subsequently the abrasive substances and portions of tissue removed which lie over the zone are sucked by the pump through the tube and conveyed to the interior of the reservoir. The cylindrical body, preferably made of electrically conductive material, houses two longitudinal parallel tubes, which have respective first ends connected to the duct and the suction pump respectively, and respective second ends, opposite the first ends, which open into a chamber delimited by the bell-like element, by a block fixed to the body by means of a screw and supporting the second end of the tube, and by a nozzle maintained in position around the second end of the tube by the block. The preferred hand tool for use in the present invention is described in detail in U.S. Pat. No. 5,037,432 (Molinari), which disclosure is incorporated by reference herein.

The invention being thus described, it will be obvious that the same may be varied in many ways. Such variations are not to be regarded as a departure from the spirit and scope of the invention and all such modifications are intended to be included within the scope of the following claims.

We claim:

1. A cartridge for use in a dermal abrasion system comprising:
   (a) a supply compartment having a top, bottom, front, and a back side, wherein the front side of the supply compartment comprises an air inlet fitting for introducing air into the supply compartment and the bottom side of the supply compartment comprises a feed tube fitting; and
   (b) a waste compartment having a top, bottom, front, and a back side, wherein the front side of the waste compartment comprises a vacuum inlet fitting for introducing vacuum into the waste compartment and the front side of the waste compartment comprises a return tube fitting.

2. The cartridge according to claim 1, wherein the air inlet fitting in the supply compartment comprises multiple air intake holes.

3. The cartridge according to claim 1, wherein the air inlet fitting in the supply compartment comprises an air intake filter.

4. The cartridge according to claim 1, wherein the sides of the supply compartment slope inwardly.

5. The cartridge according to claim 1, wherein the feed tube fitting in the supply compartment comprises a seal.

6. The apparatus according to claim 1, wherein the supply compartment further comprises a granular abrasive substance.

7. The cartridge according to claim 1, wherein the vacuum inlet fitting in the waste compartment comprises an air outtake filter.

8. The cartridge according to claim 1, wherein the sides of the waste compartment slope inwardly.

9. The cartridge according to claim 1, wherein the supply compartment and the waste compartment are transparent.

10. The cartridge according to claim 1, wherein the supply compartment and the waste compartment are attached to each other.

11. The cartridge according to claim 1, further comprising a hand tool connected to the feed tube fitting through a duct, wherein the hand tool comprises an elongated manipulative body, a supply tube for a mixture of air and a granular abrasive substance, a collection tube for vacuuming in the mixture and removed portions of skin, each tube having a terminal portion with a free end, and an operating head secured to the manipulative body at the distal end and housing the terminal portions, the body housing the other portion of the tubes, the head having a longitudinal axis and being provided with a wall having a wall portion inclined and offset with respect to the axis, a throughhole being provided in the wall portion and internally communicating with the free ends of the terminal portions, the throughhole being aligned with the terminal portion of the supply tube so that, by keeping in contact the throughhole with the surface, the stream of mixture travelling through the terminal portion of the supply tube and the throughhole is caused to strike the surface with an inclined incident angle.

12. An apparatus for use in a dermal abrasion system comprising:
   (A) a cartridge comprising:
      (a) a supply compartment having a top, bottom, front, and a back side, wherein the front side of the supply compartment comprises an air inlet fitting for introducing air into the supply compartment and the bottom side of the supply compartment comprises a feed tube fitting; and
      (b) a waste compartment having a top, bottom, front, and a back side, wherein the front side of the waste compartment comprises a vacuum inlet fitting for introducing vacuum into the waste compartment and the front side of the waste compartment comprises a return tube fitting;
   (B) a granular abrasive substance inside the supply compartment;
   (C) a vacuum supply attached to the vacuum inlet fitting of the waste compartment;
   (D) a hand tool to be applied to the surface of skin attached to the feed tube fitting of the supply compartment; and
   (E) duct means from the feed tube fitting to the hand tool for conveying a mixture of air and granular abrasive substance from the supply compartment to the hand tool, duct means from the hand tool to the return tube fitting for conveying a mixture of air and granular abrasive substance and removed portions of skin waste from the hand tool to the waste compartment, and duct means from the vacuum inlet fitting in the waste compartment to the vacuum supply.

13. The apparatus according to claim 12, wherein the air inlet fitting in the supply compartment comprises multiple air intake holes.

14. The apparatus according to claim 12, wherein the air inlet fitting in the supply compartment comprises an air intake filter.

15. The apparatus according to claim 12, wherein the sides of the supply compartment slope inwardly.

16. The apparatus according to claim 12, wherein the vacuum inlet fitting in the waste compartment comprises an air outtake filter.

17. The apparatus according to claim 12, wherein the sides of the waste compartment slope inwardly.

18. The apparatus according to claim 12, wherein the supply compartment and the waste compartment are transparent.

19. The apparatus according to claim 12, wherein the supply compartment and the waste compartment are attached to each other.

20. The apparatus according to claim 12, wherein the hand tool comprises an elongated manipulative body, a supply tube for a mixture of air and a granular abrasive substance, a collection tube for vacuuming in the mixture and removed portions of skin, each tube having a terminal portion with a free end, and an operating head secured to the manipulative body at the distal end and housing the terminal portions, the body housing the other portion of the tubes, the head having a longitudinal axis and being provided with a wall having a wall portion inclined and offset with respect to the axis, a throughhole being provided in the wall portion and internally communicating with the free ends of the terminal portions, the throughhole being aligned with the terminal portion of the supply tube so that, by keeping in contact the throughhole with the surface, the stream of mixture travelling through the terminal portion of the supply tube and the throughhole is caused to strike the surface with an inclined incident angle.

21. A method for removing debris in a dermal abrasion system which comprises the steps of:
   (1) providing an apparatus comprising:
      (A) a cartridge comprising:
         (a) a supply compartment having a top, bottom, front, and a back side, wherein the front side of the supply compartment comprises an air inlet fitting for introducing air into the supply compartment and the bottom side of the supply compartment comprises a feed tube fitting; and
         (b) a waste compartment having a top, bottom, front, and a back side, wherein the front side of the waste compartment comprises a vacuum inlet fitting for introducing vacuum into the waste compartment and the front side of the waste compartment comprises a return tube fitting;
      (B) a granular abrasive substance inside the supply compartment;
      (C) a vacuum supply attached to the vacuum inlet fitting of the waste compartment;
      (D) a hand tool to be applied to the surface of skin attached to the feed tube fitting of the supply compartment; and
      (E) duct means from the feed tube fitting to the hand tool for conveying a mixture of air and granular abrasive substance from the supply compartment to the hand tool, duct means from the hand tool to the return tube fitting for conveying a mixture of air and granular abrasive substance and removed portions of skin waste from the hand tool to the waste compartment, and duct means from the vacuum inlet fitting in the waste compartment to the vacuum supply;
   (2) applying vacuum to the vacuum inlet fitting to introduce vacuum into the waste compartment thereby drawing the granular abrasive substance in the supply compartment into the feed tube fitting and the hand tool.

22. The method according to claim 21, wherein the hand tool comprises an elongated manipulative body, a supply tube for a mixture of air and a granular abrasive substance, a collection tube for vacuuming in the mixture and removed portions of skin, each tube having a terminal portion with a free end, and an operating head secured to the manipulative body at the distal end and housing the terminal portions, the body housing the other portion of the tubes, the head having a longitudinal axis and being provided with a wall having a wall portion inclined and offset with respect to the axis, a throughhole being provided in the wall portion and internally communicating with the free ends of the terminal portions, the throughhole being aligned with the terminal portion of the supply tube so that, by keeping in contact the throughhole with the surface, the stream of mixture travelling through the terminal portion of the supply tube and the throughhole is caused to strike the surface with an inclined incident angle.

* * * * *